United States Patent [19]

Austin et al.

[11] 4,117,725
[45] Oct. 3, 1978

[54] FLUID SAMPLING SYSTEM

[75] Inventors: Robert R. Austin, Pasadena; A. M. D. Moen, Covina, both of Calif.

[73] Assignee: International Telephone and Telegraph Corporation, New York, N.Y.

[21] Appl. No.: 665,956

[22] Filed: Mar. 11, 1976

[51] Int. Cl.² .................................................. G01N 1/22
[52] U.S. Cl. .................................................. 73/421.5 R
[58] Field of Search ............... 73/421.5 R, 422 TC, 73/422 GC; 137/488, 539

[56] References Cited

U.S. PATENT DOCUMENTS

| | | | |
|---|---|---|---|
| 3,056,423 | 10/1962 | Leiser | 137/539 X |
| 3,321,977 | 5/1967 | Topham | 73/422 GC |
| 3,722,534 | 3/1973 | Breunich et al. | 137/488 |
| 3,733,907 | 5/1973 | Briggs | 73/421.5 R |
| 3,819,330 | 6/1974 | Creighton | 73/421.5 A |
| 3,881,505 | 5/1975 | Dunkelis | 137/488 X |

*Primary Examiner*—S. Clement Swisher
*Attorney, Agent, or Firm*—A. Donald Stolzy

[57] ABSTRACT

A system for sampling flue gases for a Klaus process controller by periodically capturing flue gas in a sample chamber with one side closed and the other side open, closing the other side, and only thereafter exposing the other side to a carrier fluid having a constant rate of flow. The carrier fluid and flue gas thus mix and are subsequently scrubbed and fed to the balance of the controller apparatus. The sample chamber is opened and closed by metal bellows operated valves selectively provided with positive and negative (vacuum) interior pressures in a certain sequence.

15 Claims, 4 Drawing Figures

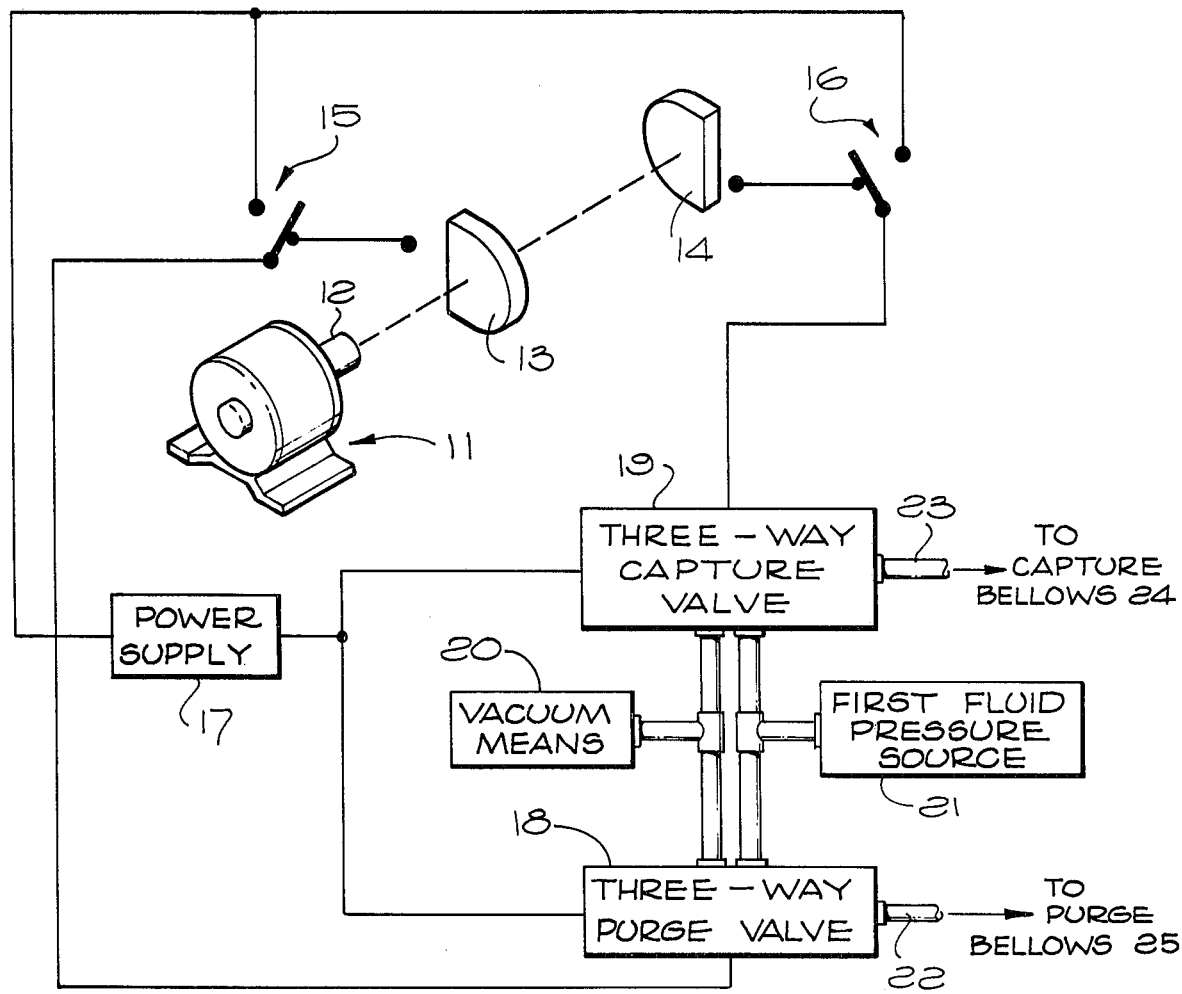
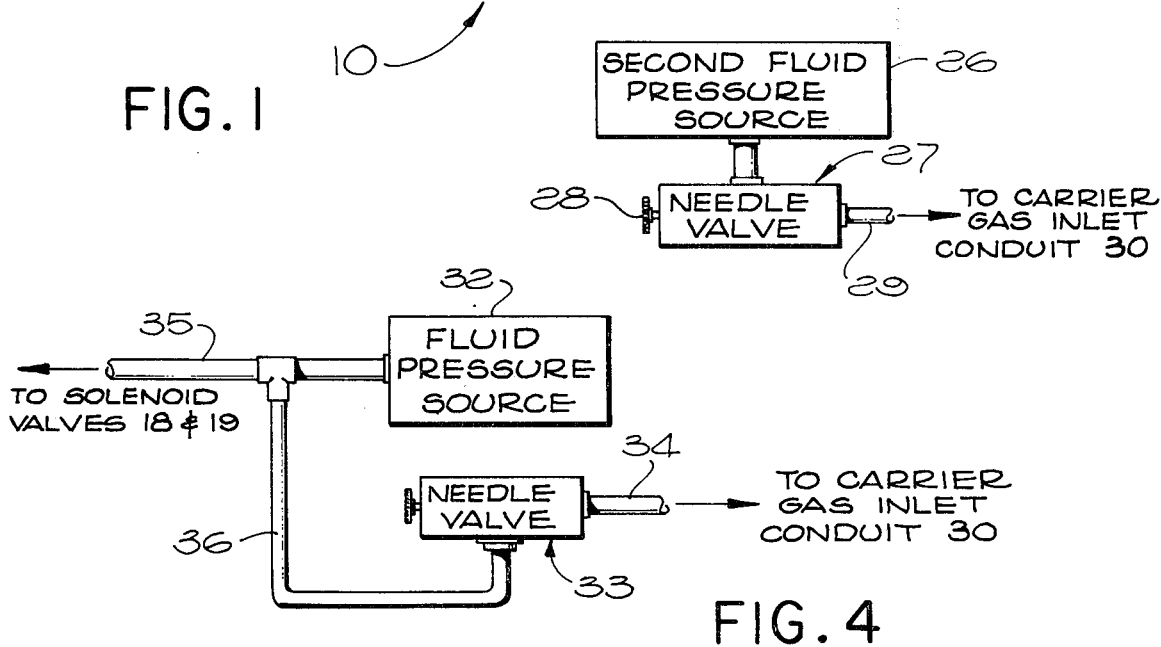
FIG. 1
FIG. 4

FLUID SAMPLING SYSTEM

BACKGROUND OF THE INVENTION

This invention relates to the fluid handling art, and more particularly to a fluid sampler.

In the past, fluid samplers for flue gas have been employed in larger systems such as Klaus process controllers of the type disclosed in U.S. Pat. No. 3,854,884 issued Dec. 17, 1974. Unfortunately those samplers, which utilize piston type slide valves, often become inoperative in a very short time. They must be cleaned. Further, they have a very short life. This is true because particulates in stack gases clog valve ports, the valve itself, and sliding fluid tight seals therein. Moreover, hydrogen sulfide ($H_2S$) gas in the stack causes seal deterioration and leakage because $H_2S$ gas reacts adversely with natural and synthetic rubber, and with other seal materials. Although seal rubbing action alone creates wear, in combination with the $H_2S$ gas the wear is very much accelerated, and seal deterioration is otherwise accelerated as well.

SUMMARY OF THE INVENTION

In accordance with the fluid sampling system of the present invention, the above-described and other disadvantages of the prior art are overcome by providing a fluid sampler in which a portion of a fluid to be sampled is captured in a sample chamber by closing one end thereof while the other end is closed. The other end is then opened and the portion purged by a carrier fluid.

In accordance with certain outstanding features of the present invention, the sample chamber may be opened and closed by ball valves providing metal-to-metal seals and operated by positive and negative (vacuum)fluid pressure inside metal bellows.

In accordance with the foregoing, the prior art problems with slide valves are overcome by the use of ball valves with metal-to-metal seals. The present invention thus is wear resistant and has a long life because the seals thereof have no sliding movement or rubbing action. Cleaning is also seldom necessary because the ball valves are self-cleaning. Further, there are no moving parts in the stack except the ball valves and the bellows.

There are no soft seals in the present invention near the fluid sample chamber or the sample fluid to be attacked by concentrated $H_2S$ gas or other gaseous elements and/or compounds and/or mixtures thereof. The hard seals of the present invention thus last, do not deteriorate at an accelerated rate, and provide more than adequate protection against substantial leakage. The metal seals of the present invention also wear and/or deteriorate very slowly.

The above-described and other advantages of the present invention will be better understood from the following detailed description when considered in connection with the accompanying drawings.

BRIEF DESCRIPTION OF THE DRAWINGS

In the drawings which are to be regarded as merely illustrative:

FIG. 1 is a block diagram of a fluid control apparatus;

FIG. 4 is a block diagram of an alternate embodiment of the present invention.

DESCRIPTION OF THE PREFERRED EMBODIMENTS

Figure 2:
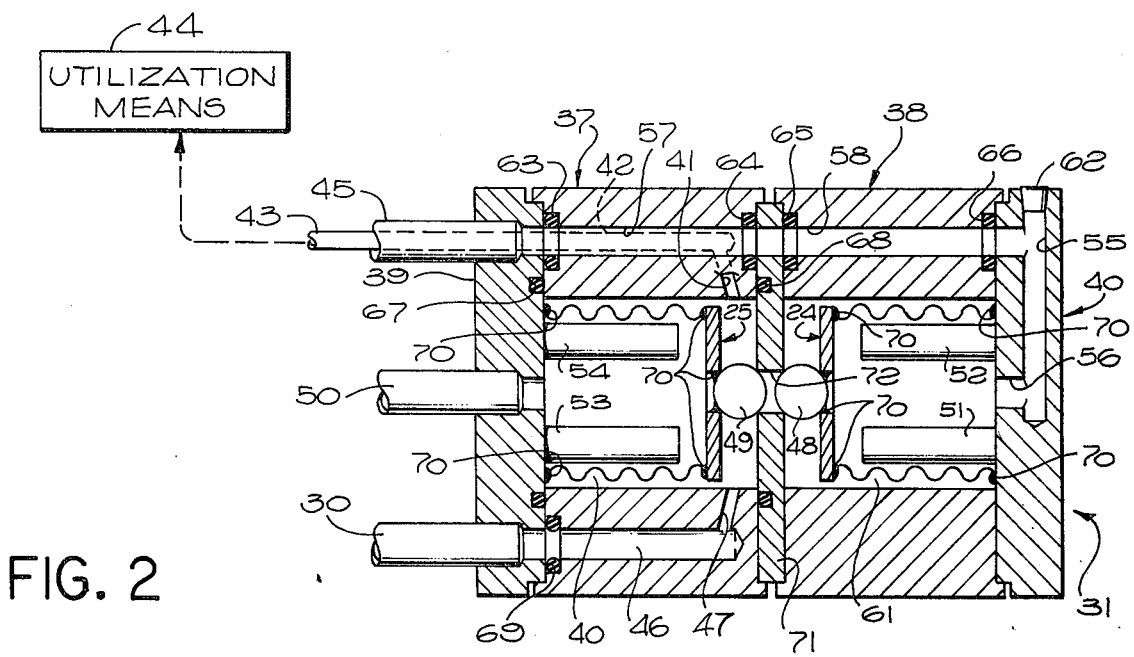
FIG. 2 is a longitudinal sectional view through apparatus controlled by that shown in FIG. 1, the apparatus shown in FIGS. 1 and 2 forming a fluid sampling system constructed in accordance with the present invention.

Control apparatus 10 is shown in FIG. 1 including a motor 11 having an output shaft 12 that may rotate at, for example, 1 revolution per second. Shaft 12 rotates cams 13 and 14 to close single-pole, single-throw switches 15 and 16, respectively, in a predetermined sequence and for periods of time to be described.

From a power supply 17, switch 16 operates a three-way valve 19. Both of the valves 18 and 19 are connected from vacuum means 20 and a first fluid pressure source 21. The outputs of valves 18 and 19 are illustrated at 22 and 23 and are conduits having their interiors in communication with the interiors of bellows 25 and 24, respectively, shown in FIG. 2. A second fluid pressure source is provided at 26 in FIG. 1 that is connected to needle valve 27 having an adjustable knob 28. Needle valve 27 has an outlet conduit 29 connected to an inlet conduit 30 of the apparatus 31 to be controlled shown in FIG. 2.

An alternative method of providing a carrier gas is illustrated in FIG. 4 where a fluid pressure source 32 provides gas for valves 18 and 19 as well as carrier gas. A needle valve is provided at 33 as before with an outlet conduit 34 for connection with inlet conduit 30 shown in FIG. 2. Fluid pressure source 32 has an outlet conduit 35 for connection to valves 18 and 19, and an outlet conduit 36 which is connected to the inlet of needle valve 33.

All the structure illustrated in FIG. 1 may be located outside a flue.

The structure shown in FIG. 2 is mounted inside a flue. Apparatus 31 in FIG. 2 includes hollow cylinders 37 and 38 which are concentric about the same axis, and end covers 39 and 40. The outlet of apparatus 31 is taken from a chamber 40, in which bellows 25 is located, through a port 41 and thence through a passage 42 in body 37 and cover 39 and outwardly of a conduit 43 to a utilization means 44. Conduit 43 is not inside a conduit 45, but is to the rear thereof, as shown in FIG. 2.

Carrier gas, which may be clean, filtered air, is supplied through inlet conduit 30 and arrives in chamber 40 through passage 46 and a port 47.

Each bellows 24 and 25, which may be referred to herein as capture bellows 24 and purge bellows 25, respectively, have ball valves 48 and 49 movable to the right and to the left, respectively, as viewed in FIG. 2.

Operating air from purge valve 18 taken from outlet conduit 22 thereof is introduced to and withdrawn from bellows 25 by an inlet conduit 50. Bellows 24 may be guided by rods 51 and 52, if desired. Bellows 25 may be guided by rods 53 and 54.

Bodies 37 and 38 have aligned passageways 57 and 58 through which air is injected into and withdrawn from bellows 24 by conduit 45 which is connected from capture valve outlet conduit 23 shown in FIG. 1. The air injected into and evacuated from bellows 24 also passes through a passageway 55 and a port 56.

Figure 3:
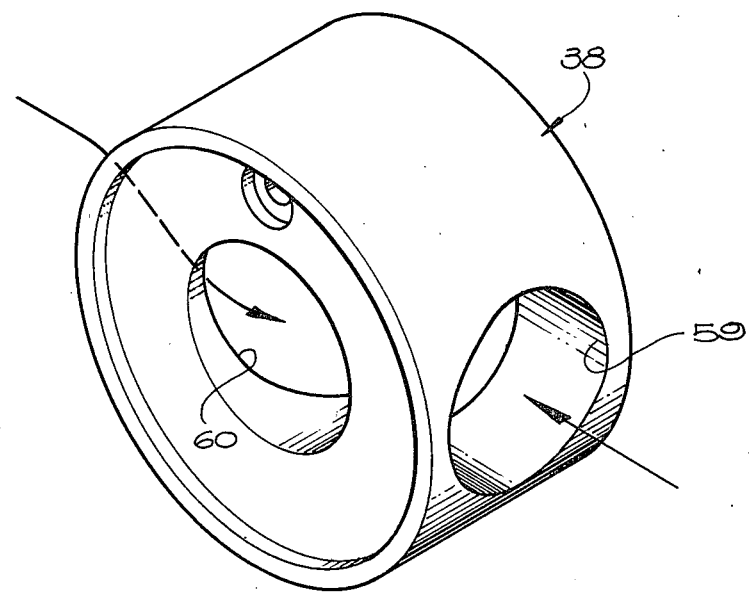
FIG. 3 is a perspective view of a portion of the apparatus shown in FIG. 2.

As shown in FIG. 3, body 38 has holes 59 and 60 through which stack gases may enter into a chamber 61 shown in FIG. 2 in which bellows 24 is located.

A welded plug 62 seals the upper end of passage 55 in cover 40 as shown in FIG. 2.

Teflon seals or seals of other materials and grooves therefor are provided at 63, 64, 65, 66, 67, 68 and 69.

Note will be taken that no soft seals are exposed to the stack gases in chamber 61.

A vacuum means 20 shown in FIG. 1 may be a vacuum pump or other equivalent device. All the structures shown in FIG. 1 may be individually conventional, but, in combination, are new. The same is true of the component parts of apparatus 31 shown in FIG. 2 and the arrangement of FIG. 4.

If desired, the carrier air may be filtered, sulfur-free, clean air flowing at a rate of 500 cubic centimeters per minute. The air pressure of the carrier air may be from 5 psi to 10 psi.

The materials of apparatus 31 in FIG. 2, except for the welds 70, which may be conventional, may be made of many conventional materials, but are preferably made of 316 stainless steel, monel, or metals non-corrosive to $H_2S$ or other elemental gases, gas compounds or gas mixtures of interest.

Ball valves 48 and 49 are preferably made of or plated with chrome or other materials employed with ball valves.

Utilization means 44 shown in FIG. 2 may be any device with utilizes the sampled stack gas and may be a Klaus process controller as disclosed in the said patent.

The word "fluid" is defined for use herein and for use in the claims to mean an elemental gas, a gas compound, or a mixture of one or more elemental gases and/or one or more gas compounds in any combination, unless the invention is operative with liquids or other fluids.

The phrase "carrier injection means" is hereby defined for use herein and for use in the claims to mean a conduit, pump or otherwise.

The phrase "utilization means" is hereby defined for use herein and for use in the claims to mean a coulometric titrator, an indicator, a Klaus or other process controller, or otherwise.

The vacuum provided by vacuum means 20 is not critical but preferably is about 15 inches of mercury.

In order to be able to operate bellows 24 and 25 with the least possible pressures, preferably the following instructions are to be followed. In the first place, the pressures inside the bellows 24 and 25 are alternately positive and negative (vacuum). When the pressures inside the bellows 24 and 25 are equal to those outside thereof, and the bellows are thereby not subjected to any strain, valves 48 and 49 are preferably partly open. In some cases, it may be desirable to have this "rest" position of the bellows 24 and 25 midway between their extreme limits of travel when they are completely closed and completely open. The travel of each of the bellows 24 and 25 may be 80 mils from a full closed position to a full open position. Note will be taken in FIG. 2 that a partition 71 is sandwiched between bodies 37 and 38, and is provided with a hole 72 therethrough, the right end of which is or can be closed by ball valve 48, and the left end of which is or can be closed by ball valve 49. In the position shown, both valves 48 and 49 are in their closed positions which, with the internal cylindrical surface defining hole 72, provides a sample chamber.

In FIG. 1, or in FIG. 4, the pressure sources 21, 26 and 32 may be optional, or vacuum means 20 may be optional if one or both of the bellows 24 and 25 are provided with a biasing spring or are self biasing. Note will be taken that the entire interiors of chambers 40 and 61 are defined only by metal surfaces, the bellows 24 and 25 being made entirely of metal, as well as the ball valves 48 and 49.

OPERATION

In the operation of the embodiment of the invention illustrated in FIGS. 1, 2 and 3, motor 11 operates purge and capture valves 18 and 19, respectively, so that purge valve 18 connects source 21 to the interior of bellows 25 to hold ball valve 49 closing hole 72 in the position shown in FIG. 2.

In FIG. 1, shaft 12 then turns cam 14 to close switch 16 and connect the interior of bellows 24 to vacuum means 20. This opens ball valve 48, and stack gases fill the sample chamber in hole 72. Ball valve 49 then remains closed all this time and for a further period during whih ball valve 48 is moved to the closed position shown in FIG. 2 by the removal of vacuum means 20 from inlet conduit 45 shown in FIG. 2 and connecting source 21 to the interior of bellows 24 to close ball valve 48. After ball valve 48 closes, ball valve 49 is opened in a similar manner by the continued rotation of motor shaft 12 rotating cam 13 to close switch 15. The ball valves 48 and 49 are operated synchronously and for periods of time and at frequencies which are substantially constant. The flow of carrier fluid through inlet 30 in FIG. 2 is also maintained constant to keep the volume rate of flow of both carrier fluid and the sample in hole 72 constant. After a sample of the stack gases fills hole 72 and both valves 48 and 49 are closed, ball valve 49 opens, and the carrier fluid emanating from port 47 purges hole 72 of the stack gases sampled. The mixed carrier gas (air) and the sample gas (stack gas) then exit through port 41, passage 42 and conduit 43 to utilization means 44.

What is claimed is:

1. A fluid sampling system, said system comprising: a substantially fluid tight housing having a hollow interior divided by a partition into first and second chambers, said partition having a hole therethrough; a first valve mounted on said housing and actuable to close an end of said hole opening into said first chamber; a second valve mounted on said housing and actuable to close the other end of said hole, said other hole end opening into said second chamber, said housing having spaced inlet and outlet passages opening into and out of said second chamber, respectively, for circulation of a carrier fluid through said second chamber, said housing having opening means extending therethrough into said first chamber to permit a sample fluid to flow into said first chamber; actuating means to open and to close said first valve in succession while holding said second valve closed, and vice versa, said first and second valves being spaced apart when both are closed, said first and second valves and said partition defining a closed sample chamber in said hole when said first and second valves are closed, a sample of said sample fluid being permitted to fill said sample chamber when said second valve is closed and said first valve is opened, said sample chamber being filled with said sample fluid upon closure of said first valve, subsequent opening of said second valve permitting a carrier fluid circulated through said second chamber to purge said sample chamber of said sample fluid previously trapped or captured therein, said actuating means repeating the aforesaid opening and closing of said first and second valves so as to expose a sample fluid filled sample chamber to said second chamber at regular intervals to permit purging thereof at regular intervals by a constant flow of carrier gas.

2. The invention as defined in claim 1, wherein first and second bellows each have a movable end and are positioned in said first and second chambers, respectively, the other end of each bellows being sealed to a respective housing wall around an inlet thereinto, said first and second valves being fixed to said first and second bellows movable ends, respectively, said actuating means expanding and contracting said first and second bellows to open and to close said first and second valves as aforesaid.

3. The invention as defined in claim 2, wherein said actuating means causes movement of said first and second bellows in the same or different first and second respective predetermined directions by changing the pressure inside said first and second bellows, respectively.

4. The invention as defined in claim 3, wherein said actuating means places a fluid under pressure inside of said first and second bellows to close said first and second valves, respectively, said actuating means including vacuum means to remove fluid from inside said first and second bellows to open said first and second valves, respectively.

5. The invention as defined in claim 4, wherein said first and second valves include first and second ball valves, respectively.

6. The invention as defined in claim 5, wherein first and second locator means are fixed to said housing inside said first and second bellows, respectively, to guide said first and second bellows in a manner to cause said first and second valves to seat on respective opposite ends of said hole.

7. The invention as defined in claim 6, wherein flow means are provided which are connected to said second chamber inlet to supply carrier fluid thereto at a constant flow rate, and utilization means are provided which are connected from said second chamber outlet.

8. The invention as defined in claim 7, wherein said utilization means includes a Klaus process controller.

9. The invention as defined in claim 8, wherein said first and second bellows other ends are provided with fluid tight welds to said housing.

10. The invention as defined in claim 1, werein said first and second valves include first and second ball valves, respectively.

11. The invention as defined in claim 2, wherein said first and second valves include first and second ball valves, respectively.

12. The invention as defined in claim 11, wherein first and second locator means are fixed to said housing inside said first and second bellows, respectively, to guide said first and second bellows in a manner to cause said first and second valves to seat on respective opposite ends of said hole.

13. The invention as defined in claim 3, wherein said first and second valves include first and second ball valves, respectively.

14. The invention as defined in claim 13, wherein first and second locator means are fixed to said housing inside said first and second bellows, respectively, to guide said first and second bellows in a manner to cause said first and second valves to seat on respective opposite ends of said hole.

15. The invention as defined in claim 1, wherein flow means are provided which are connected to said second chamber inlet to supply carrier fluid thereto at a constant flow rate, and utilization means are provided which are connected from said second chamber outlet.

* * * * *